(12) United States Patent
Samuelsson et al.

(10) Patent No.: US 6,579,272 B1
(45) Date of Patent: Jun. 17, 2003

(54) FORMING ELEMENT FOR AN ABSORBENT ARTICLE AND AN ABSORBENT ARTICLE CONTAINING THE SAME

(75) Inventors: Ann Samuelsson, Lindome (SE); Charlotte Persson, Göteborg (SE); Pascale Cabelduc, Göteborg (SE); Solgun Drevik, Mölnlycke (SE)

(73) Assignee: SCA Hygiene Products, Göteborg (SE)

( * ) Notice: Subject to any disclaimer, the term of this patent is extended or adjusted under 35 U.S.C. 154(b) by 0 days.

(21) Appl. No.: 09/309,283

(22) Filed: May 11, 1999

(30) Foreign Application Priority Data

May 12, 1998 (SE) ................................. 9801666

(51) Int. Cl.[7] .................................................. A61F 13/20
(52) U.S. Cl. ...................................... 604/385.1; 604/370
(58) Field of Search ........................... 604/385.1, 385.2, 604/378, 379, 380, 367, 385.08, 370

(56) References Cited

U.S. PATENT DOCUMENTS

| 4,685,914 A | * | 8/1987 | Holtman ..................... 604/368 |
| 5,300,055 A | | 4/1994 | Buell |
| 5,766,213 A | * | 6/1998 | Hackman et al. ........ 604/385.01 |
| 6,129,717 A | * | 10/2000 | Fujioka et al. ............... 604/368 |
| 6,156,951 A | * | 12/2000 | Gustafsson et al. .......... 604/369 |

FOREIGN PATENT DOCUMENTS

| WO | 93/01782 | 2/1993 |
| WO | WO 94/10956 | 5/1994 |
| WO | 98/22057 | 5/1998 |
| WO | WO 98/22058 | 5/1998 |
| WO | WO 98/22061 | 5/1998 |
| WO | WO 98/22062 | 5/1998 |
| WO | WO 99/00081 | 1/1999 |

* cited by examiner

*Primary Examiner*—Weilun Lo
*Assistant Examiner*—Michele Kidwell
(74) *Attorney, Agent, or Firm*—Burns, Doane, Swecker & Mathis, L.L.P.

(57) ABSTRACT

A forming element for an absorbent article, such as a sanitary napkin, an incontinence protector or a panty shield, which forming element is formed of a rigid material and exhibits a principally elongate form with a longitudinal direction and a transverse direction, an upper side, an underside, two short sides and two long sides, a first and a second end portion and an intermediate portion situated between the end portions, and wherein the forming element exhibits one or several corrugations.

17 Claims, 8 Drawing Sheets

US 6,579,272 B1

FORMING ELEMENT FOR AN ABSORBENT ARTICLE AND AN ABSORBENT ARTICLE CONTAINING THE SAME

TECHNICAL FIELD

The invention concerns a forming element for an absorbent article, such as a sanitary napkin, an incontinence protector or a panty shield, which forming element is formed of a rigid material and exhibits a principally elongate form with a longitudinal direction and a transverse direction, an upper side, an underside, two short sides and two long sides, a first and a second end portion and an intermediate portion.

The invention further concerns an absorbent article, such as a sanitary napkin, an incontinence protector or a panty shield, which article has a principally elongate form with two end portions and an intermediate portion situated between the end portions.

BACKGROUND

Absorbent articles, such as sanitary napkins, incontinence protectors and panty shields are subjected during use to great forces, for example when the user is walking. The absorbent article is then sheared between the thighs of the user. A conventional absorbent article is usually manufactured in soft materials, which wrinkle under the effect of these forces. Wrinkles result in a reduction of the reception area on the article for liquid which is emitted from the user. Moreover, the wrinkles form channels in which liquid on the surface of the article can run out towards and over the edges of the article. In other words, there is an increased risk of leakage.

This problem has been solved by providing the article with forming elements of shape stable material which can withstand stresses during use. Such articles are described in, for example, PCT/SE97/01881, PCT/SE97/01882 PCT/SE97/01885 and PCT/SE97/01886.

Furthermore, it is not unusual for the attachment system of the absorbent article to lead to leakage problems. Usually, absorbent articles, such as sanitary napkins, are attached in the underclothes of the user using glue. As a result, the article follows the movements of the underclothes rather than the body movements of the user. Displacements and gaps between the body of the user and the article can lead to the available reception area becoming insufficient. Moreover, liquid can leak out between the article and the body of the user.

This problem, also, is solved in the above publications by means of the physical design of the forming element in combination with the rigidity of the forming element. By forming an article in such a way that it conforms to a high degree with the body shape of the user and by ensuring that its rigidity is sufficiently high to avoid deformation, an article can remain in place during use without the need for special attachment devices. Such an article will follow the body movements of the user during use, thus considerably reducing the risk of leakage.

In order for an article to fit well and to stay in place against the body, it should not be flat, inasmuch as the anatomical parts the article is to fit against are not flat. One alternative is to give the forming element a three-dimensional form. Another way to solve the problem is to design a principally flat forming element in a principally flat article, which, due to the design of the article, becomes three-dimensional during use. An article of that kind is described in the Swedish patent application SE702463-2.

Other ways to achieve forming during use are to provide the article with folding indications, or the like.

In order to function as intended and to make the absorbent article shape stable, the forming element must be made of a rigid material and exhibit a sufficient thickness. If the forming element has a high thickness the total weight of the absorbent article will also be high. A high weight of the absorbent article can lead to problems, for instance concerning transport and user comfort.

OBJECT OF THE INVENTION

A purpose of the present invention is therefore to obtain a forming element with low weight but necessary rigidity and an absorbent article containing such a forming element.

BRIEF DESCRIPTION OF THE INVENTION

An article of the type mentioned in the introduction, with which the problems associated with previously known articles of this type have been essentially removed, is characterised, according to the invention, in that the forming element exhibits one or several corrugations.

The article preferably exhibits a ridge-like raised portion arranged on the upper side of the forming element in the longitudinal direction of the forming element in the second end portion.

The invention can be further characterised in that the corrugations are arranged in the first end portion, in the second end portion, which is intended to face backwards on the user during use, or in both end portions.

According to an alternative embodiment of the invention, the corrugations are arranged as elongate raised portions or depressions on the upper side of the forming element and exhibit a longitudinal direction and a transverse direction, wherein the corrugations are arranged with their longitudinal direction principally in the transverse direction of the forming element.

The forming element according to the invention can be further characterised in that the widest part on the first end portion is 1.5–5 times as wide as the narrowest width on the intermediate portion.

The invention also concerns an absorbent article comprising a forming element in accordance with what is stated above.

DESCRIPTION OF THE INVENTION

The above-mentioned problems are solved by means of the present invention. This is achieved by manufacturing the forming element of a relatively thin material layer and by arranging corrugations in the forming element.

A forming element according to the above-mentioned PCT/SE97/01881 is manufactured of a rigid layer, for example a plastic layer. Polystyrene or mineral-filled polypropylene with a layer thickness of at least 0.4 mm can be mentioned as examples of plastic materials which are stated as having sufficient rigidity and torsion rigidity to reach the necessary shape stability.

The shape stability of a forming element of the kind intended here must be sufficiently great to essentially enable the article to retain a predetermined and predictable form during use. Thus, it is possible to form the article in such a way that it lies in place against the body of the user during use without the need for special attachment members such as attaching glue or the like. The material stiffness of the layer material that is used in the forming element is of course significant to the shape stability of the forming element. Plastic materials with a stiffness coefficient of at least 1500 Mpa measured according to ISO 178 have been found to be usable. However, the shape stability of the forming element is determined not only by the material stiffness of the forming element but also by the shape of the forming element; the existence and location of corrugations in the forming element, especially, affect the shape stability.

A forming element in accordance with the invention can be formed of a plastic layer that is from approximately 0.2 mm to approximately 0.4 mm since it is provided with stiffening corrugations. Depending on the location and form of the corrugations, it can even, in certain cases, be possible to use plastic layers of a lesser thickness than 0.2 mm. In this context, the term corrugations denotes portions of a layer material which project out from the main plane of the material. The corrugations must be arranged in a direction that is parallel with the deformation forces that are to be counteracted by the corrugations. For example, transverse compression of an absorbent article is counteracted by arranging transverse corrugations, i.e. corrugations that extend in the transverse direction of the article.

Due to the fact that it is possible, according to the invention, to form a forming element of a thinner material whilst retaining high shape stability in the forming element, significant advantages of use are achieved regarding discretion and comfort. Corrugations are arranged in the forming element to create a greater rigidity and thereby shape stability within the portions of the forming element where high shape stability is critical to the fit and attachment of an absorbent article of which the forming element is a part.

An absorbent article of the type which is intended during use to essentially be accommodated in the crotch area of the user exhibits two end portions, intended to be directed backwards and forwards, respectively, on the user. Between the end portions there is an intermediate portion, which constitutes the transition between the two end portions and is narrower than these. The proportions between the various portions can vary somewhat between different articles, for example depending on the size of the article. However, the forward end portion is preferably approximately 1.5–5 times broader than the intermediate portion in order to prevent the article from shifting backwards on the user during use. The stiffening corrugations which, in accordance with the invention, are arranged in the forming element of the article, are principally arranged in the end portions of the article.

The corrugations in the forming element can be arranged only in the first or only in the second end portion. Alternatively, and preferably, the corrugations can be present in both end portions. In order to achieve a good effect with corrugations arranged only in one of the end portions, it can be suitable to form the forming element of a material with greater thickness in the end portion without corrugations. The thickness of the end portion without corrugations should then be greater than approximately 0.4 mm. However, such an embodiment is less preferable as it is more difficult to manufacture and gives the article a greater weight and reduced comfort.

The corrugations can be formed as elongate raised portions or depressions in the upper side of the forming element. The term the upper side of the forming element relates to that side of the forming element which, when it is arranged in an absorbent article, is intended to face towards the body of the user during use. The corrugations can also be formed as raised or depressed continuous areas with another suitable form. It has been shown that a plurality of separate corrugations arranged over a certain area on the forming element give a greater stiffening effect than arranging one continuous corrugation over a corresponding area.

Further, it can be advantageous to combine raised and depressed corrugations within the same area of the forming element.

The corrugations in the first end portion can be constituted of a raised or depressed area with a surface of approximately $5\times3$ cm$^2$±5 cm$^2$.

The corrugations can also be constituted of two or more elongate raised portions or depressions in the upper side of the forming element. These are arranged with their longitudinal direction principally in the transverse direction of the forming element. The corrugations can be separate or continuous in a curve, for example in an S-shape. The first end portion of the forming element is preferably formed with increasing width towards the short end of the forming element. The length of the corrugations follows the width of the end portion, i.e. they are longer the nearer they are located to the short side of the forming element. The elongate corrugations suitably have a height, or a depth, measured from the plane of the forming element that is from approximately 1.5 to 5 mm and a width that is from approximately 0.3 mm to 10 mm, preferably approximately 0.5 mm. The length can vary within fairly wide limits and can be from approximately 0.8 cm to 8 cm.

Furthermore, the corrugations do not require to have the same height along their entire length; the height can vary. For example, the corrugations can be higher at the outer edges of the forming element and lower therebetween, or vice versa.

The corrugations in the second end portion exhibiting the ridge-like raised portion can be constituted of a continuous raised area symmetrically arranged on either side of the ridge-like raised portion. The corrugations can also be formed as elongate raised portions with their longitudinal direction principally in the transverse direction of the forming element, i.e. extending across the ridge-like raised portion. The elongate corrugations in the second end portion can be, for example, 3–10 in number and can extend on one or both sides of the ridge-like raised portion. Such elongate corrugations suitably have a height or a depth that is approximately 1.5–5 mm, a width that is approximately 0.3–10 mm and a length that is approximately 0.8–20 mm.

By arranging corrugations which end a distance within the edge portions of the forming element, a deformation zone in the forming element is obtained nearest the edge. Such an embodiment can be advantageous from the point of view of comfort but can also be utilised to achieve a forming effect. For example, transverse corrugations arranged in the first portion of the forming element, i.e. that portion which is intended to be directed forwards on a user during use, can, in this way, be used to create an indication to form a cup-shape during use.

The length of the corrugations follows the contour of the forming element, i.e. a corrugation is longer in the wider part of the forming element and shorter in the narrower part.

Due to the fact that the intermediate portion is essentially free of corrugations, an article containing such a forming element can be formed flat and can then be given an anatomically correct form under the influence of the compressing forces to which the article is subjected during use. An article that is formed in this manner during use is described in SE 9702463-2.

By arranging the corrugations in the first end portion so that they follow the contour of the forming element and by making the corrugations end a distance within the side edge of the forming element, the forming element will be perfectly formed to a cup around the mons veneris of the user during use.

An absorbent article in accordance with the invention preferably exhibits a central longitudinal raised portion in that end portion which is intended to be directed backwards on a user during use. Such a raised portion can be wholly or partially formed by the forming element. Moreover, the raised portion can be wholly or partially constructed of other materials, for example absorbent materials. It is also possible to create raised portions that are not activated until the article is used, by means of folding indications in the forming element and/or the absorbent body of the absorbent article.

BRIEF DESCRIPTION OF THE FIGURES

The invention will be described below in more detail with reference to the embodiments shown in the drawings.

DETAILED DESCRIPTION OF FIGURES AND EMBODIMENTS

Figure 1:
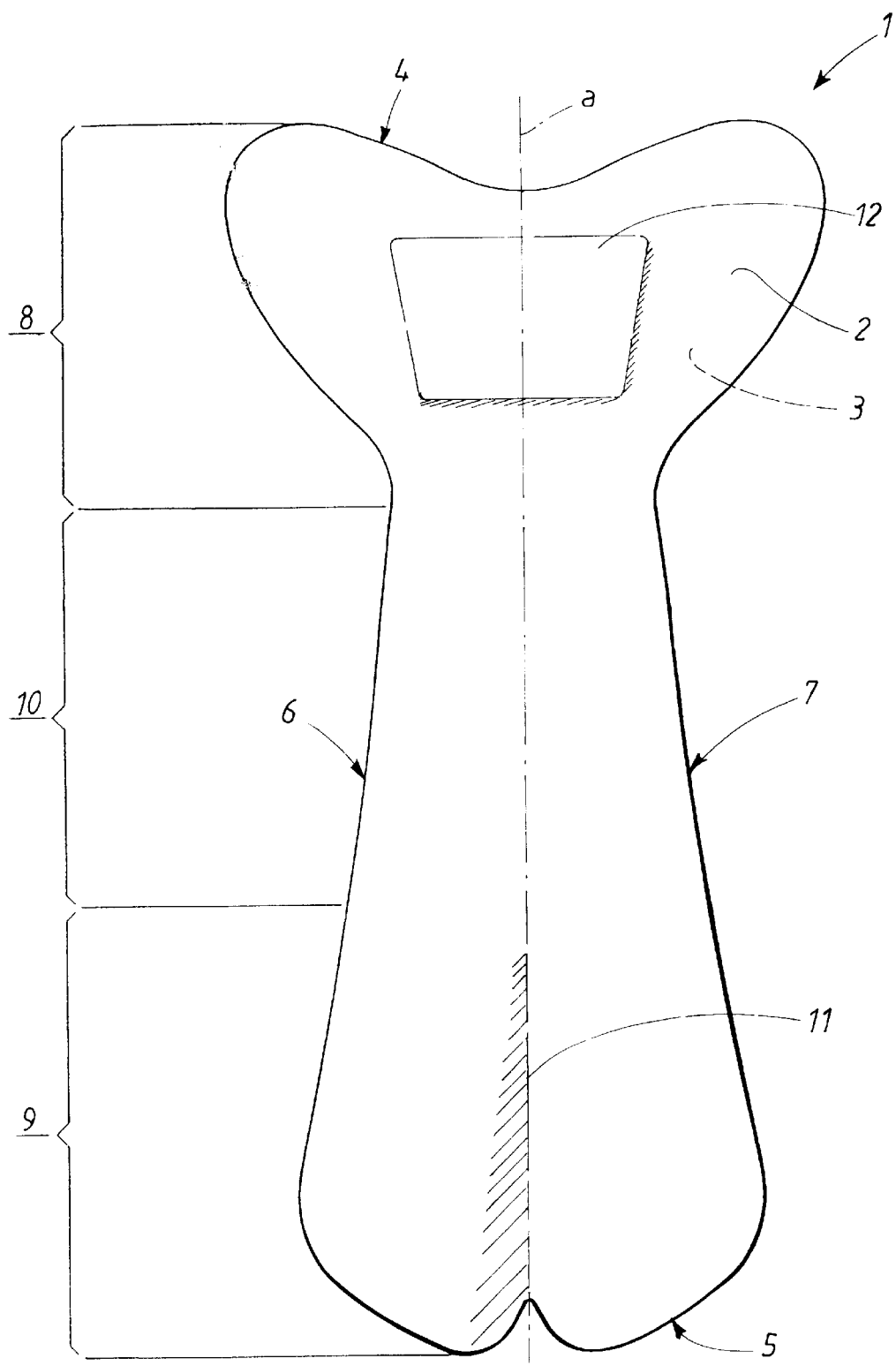
FIG. 1 shows a forming element in accordance with the invention.

FIG. 1 shows a forming element 1 in accordance with the invention. The forming element exhibits a principally elongate form with a longitudinal direction and a transverse direction, an upper side 2, an underside 3, two short sides 4, 5 and two long sides 6, 7 a first and a second end portion 8, 9, an intermediate portion 10 and a ridge-like raised portion 11 arranged on the upper side 2 in the longitudinal direction of the forming element in second end portion 9.

The forming element further exhibits a corrugation 12 in the first end portion 8. The corrugation 12 consists of a raised area on the upper side 2 of the forming element and has the form of a parallel trapezium.

The form of the corrugation 12 is adapted to the form on the outer contour of the forming element 1, i.e. the longest transverse edge on the corrugation is situated nearest the short side 4 of the forming element, where the forming element is widest.

Figure 2:
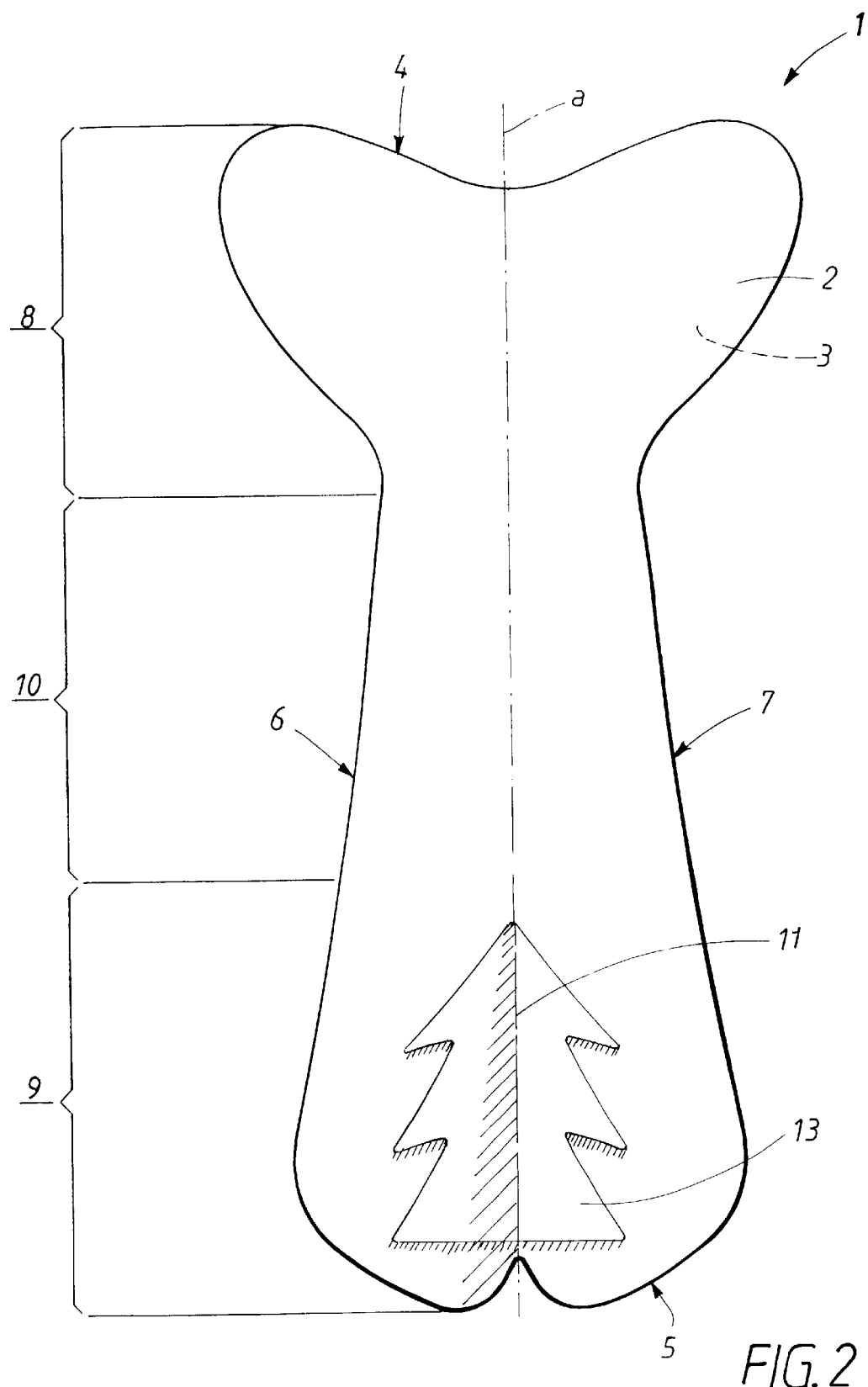
FIG. 2 shows a forming element in accordance with an alternative embodiment of the invention.

FIG. 2 shows a forming element 1 in accordance with an alternative embodiment of the invention. The forming element 1 exhibits here a corrugation 13 in the second end portion 9. The corrugation 13 is constituted by a raised portion in the form of an area which is symmetrically formed around the ridge-like raised portion 11. The corrugation 13 has symmetrical projections on either side of the ridge-like raised portion 11 and has principally the form of a Christmas tree.

The forming element can have, for example, a length that is approximately 200 mm measured along a longitudinal central line, a, of the forming element. Longitudinal central line denotes a line in the longitudinal direction of the forming element, which is situated at an equal distance from the longitudinal edges of the forming element. The first end portion contitutes approximately 50 mm of it, the second end portion constitutes ca. 100 mm of it and the intermediate portion constitutes ca. 50 mm of the total length of the forming element. The first end portion 8 exhibits a heart-shape with a width which increases in a direction towards the short side of the forming element. Where the first end portion is narrowest, in the transition between the intermediate portion 10 and the end portion 8, the first end portion is approximately 20 mm wide. At the widest part, the first end portion is approximately 90 mm wide. The intermediate portion 10 is narrowest in the transition between it and the first end portion 8 and is approximately 20 mm wide there, increasing in width towards the second end portion 9 where the width of the intermediate portion 10 is approximately 30 mm at its widest. The width of the second end portion 9 in the part which borders on the intermediate portion 10 is consequently approximately 30 mm. The width of the second end portion 9 increases from the intermediate portion 10 towards the short side of the forming element for approximately ⅔ of the length of the end portion 9 then having a more or less constant width of approximately 65 mm for the final third. The rear widening of the forming element helps to prevent the article from slipping forwards between the legs of the user. The second end portion 9 exhibits an indentation in the side which faces towards the short side 4 of the article. The purpose of this indentation is to make the article more comfortable for the user as too long an extension of the forming element in the rear end can cause discomfort and make the article less discrete.

It has been found that, in order for an absorbent article comprising a forming element in accordance with the invention to have sufficient shape permanence and to be able to be held in place against the body of a user during use, the plastic material requires to have a certain minimum stiffness. Plastic layers with a stiffness coefficient of at least 1500 Mpa measured according to ISO 178 have been found to work well. Examples of plastic materials that can be used are polystyrene and mineral-filled polypropylene. When corrugations 12, 13 are arranged in the end portions 8, 9 of the forming element 1, sufficient shape stability can be achieved for plastic layers with a thickness less than approximately 0.4 mm preferably over 0.2 mm. A thinner plastic material generally requires more and/or larger corrugations within a certain area in order to achieve a sufficient stiffening effect. Sufficient shape stability and deformation resistance are considered to be present if the absorbent article can be held in place against the body of the user during use without special attachment arrangements.

Figure 3:
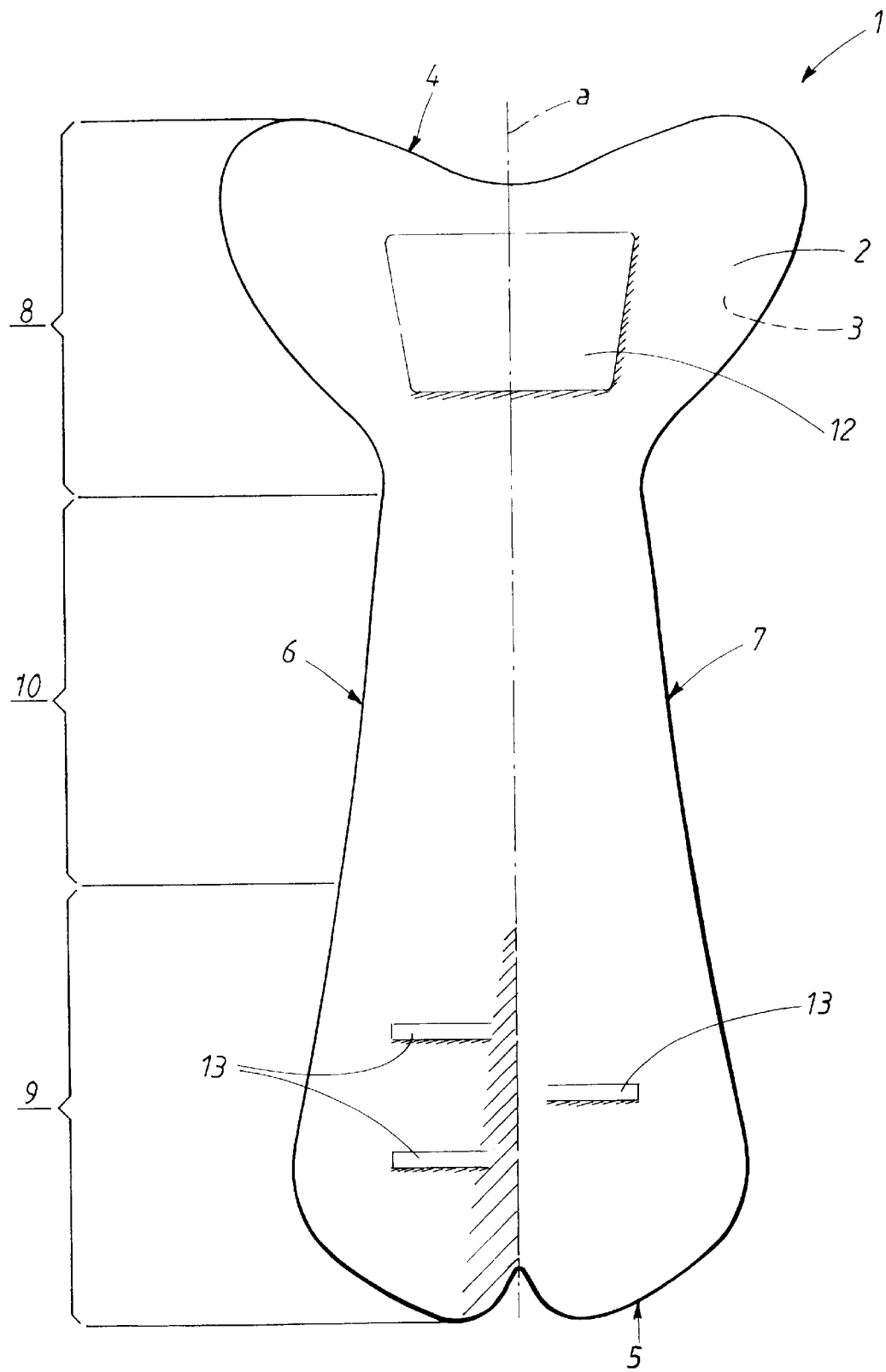
FIG. 3 shows a forming element according to a further alternative embodiment of the invention.

FIG. 3 shows a further embodiment of the invention. The forming element 1 exhibits corrugations 12, 13 in the first end portion 8 and the second end portion 9. The corrugation 12 in the first end portion 8 consists of a parallel trapezium-shaped, raised area on the upper side 2 of the forming element. The corrugations 13 in the second end portion 9 are constituted of three elongate raised portions in the upper side 2 of the forming element. The raised portions are arranged on either side of the ridge-like raised portion 11, with the longitudinal direction of the corrugations 13 arranged principally in the transverse direction of the forming element.

Figure 4A:
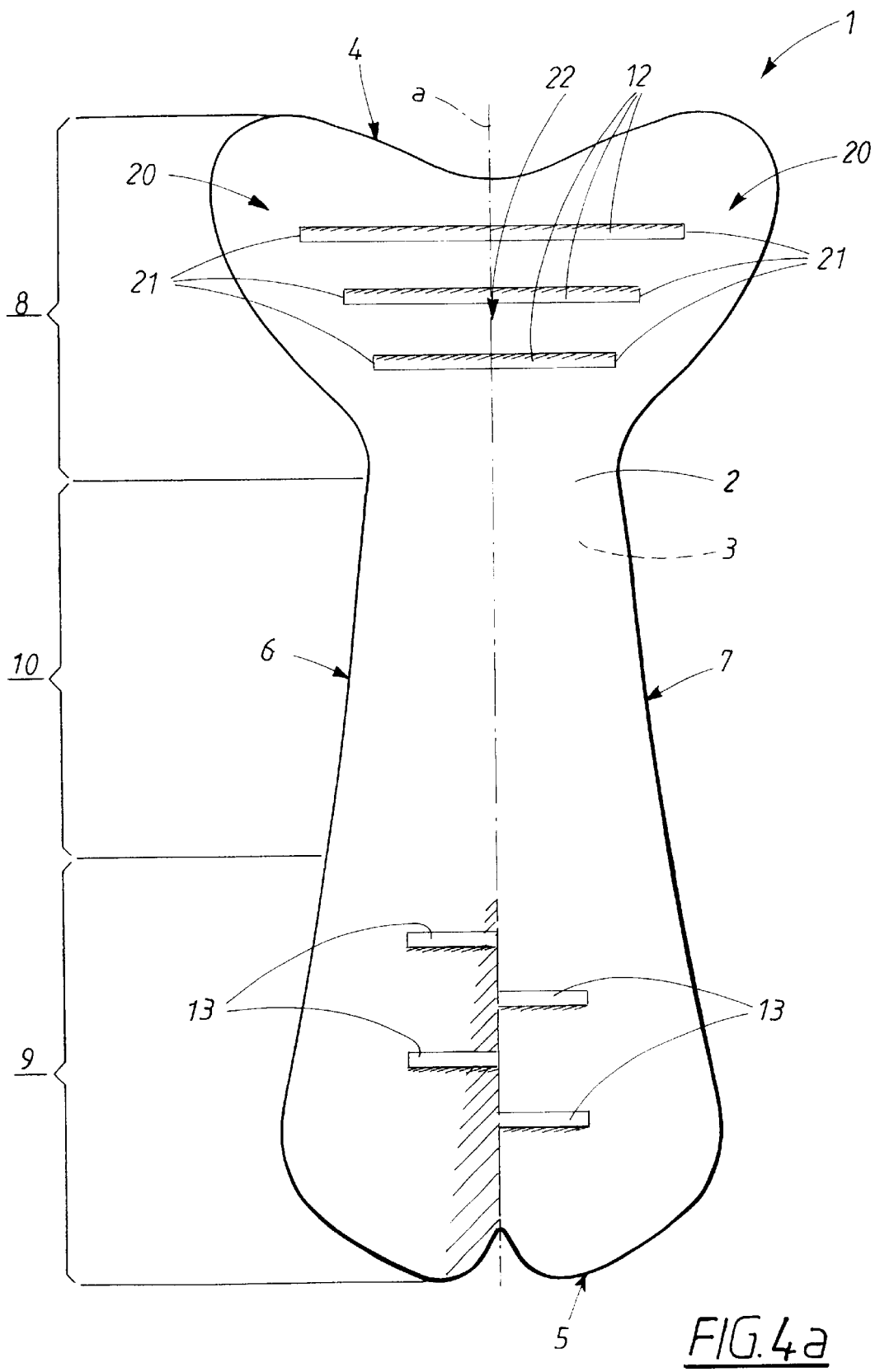
FIG. 4a shows a forming element in accordance with a further alternative embodiment of the invention.
Figure 4B:
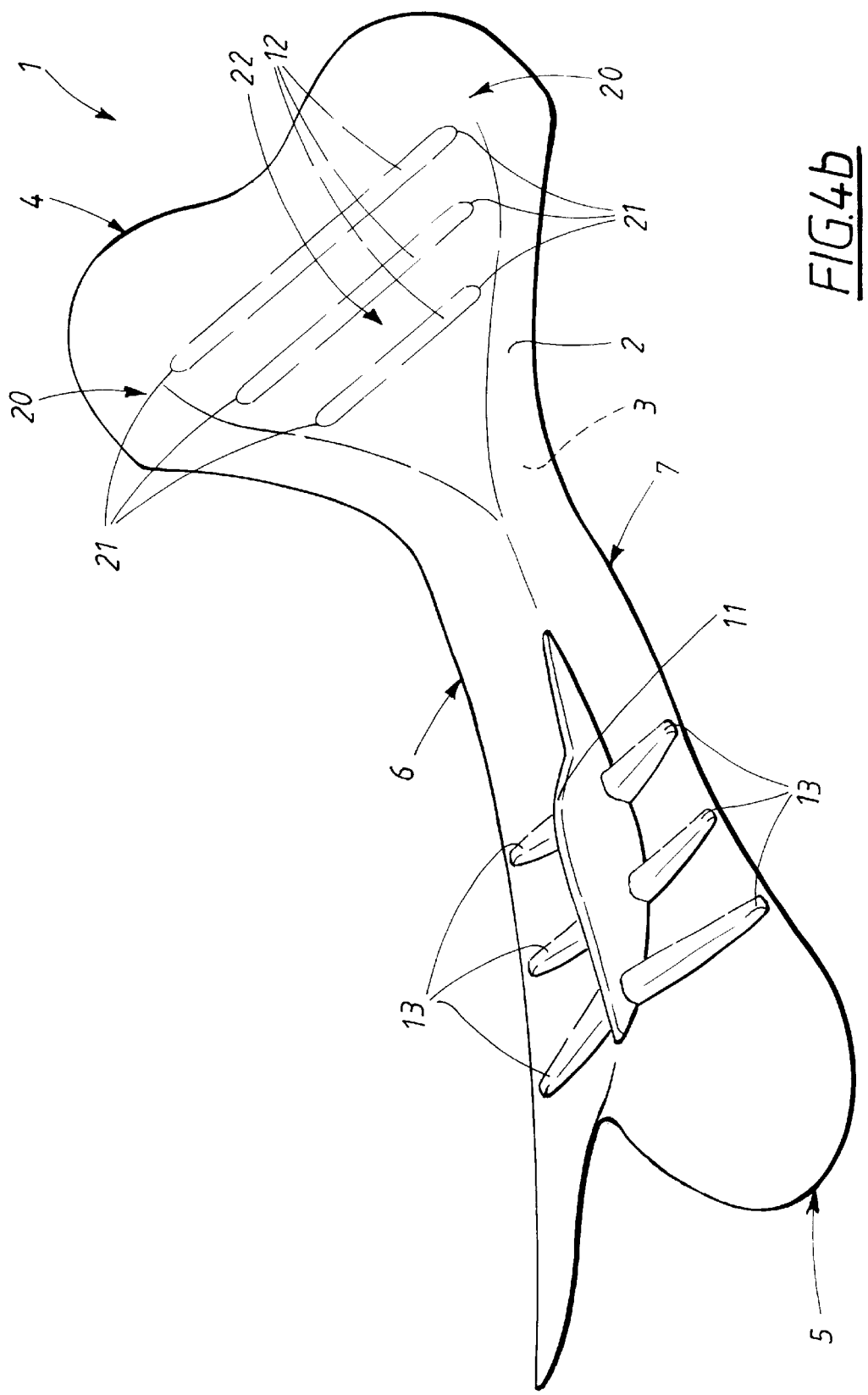
FIG. 4b shows a forming element similar to that in FIG. 4a as it appears during use

FIGS. 4a and 4b show two somewhat different embodiments of the invention in which the forming element 1 exhibits corrugations 12 in the first end portion 8. In FIG. 4a the corrugations are constituted of three elongate depressions in the upper side 2 of the forming element, while the corrugations 12 in FIG. 4b are constituted of three elongate raised portions. The corrugations 12 are arranged with their longitudinal direction in the transverse direction of the forming element. The length of the corrugations is adapted to the width of the first end portion. That is to say, as the width of the end portion diminishes in a direction from the short side 4 of the forming element towards the intermediate portion 10, the corrugations 12 become shorter the nearer they are situated to the intermediate portion 10.

A particular advantage of arranging the corrugations 12 in a pattern of the kind shown in FIGS. 4a and 4b is that, in addition to forming stiffening members which counteract undesired deformation of the central part of the first end portion 8, the corrugations 12 also serve as forming members to build a cup-shape which can conform to the contours of the mons veneris of the user during use. Such a cup-shape is shown in FIG. 4b. As the corrugations 12 only extend in the transverse direction over the central part 22 of the first end portion 8, less stiff edge portions 20 are left free of corrugations at the first short side 4 and long sides 6, 7 of the forming element 1. During use, the end edges 21 of the corrugations 12 serve as folding indications for the edge portions 20 so that these can be folded up from the upper side 2 of the forming element 1 and form cupped walls around the central part of the first end part 8. In order to achieve the desired cupping effect, the corrugation-free edge portions 20 of the forward end portion 8 should have a width between the end edges 21 of the corrugations and the long sides 6, 7 of the first end portion 8 that is at least approximately 5 mm and preferably between approximately 7 mm and 25 mm.

In FIG. 4a the second end portion 9 exhibits four corrugations 13 in the form of elongate raised portions, two of which are arranged on one side of the ridge-like raised portion and two on the other side of the raised portion. The corrugations are arranged with their longitudinal direction in the transverse direction of the forming element.

FIG. 4b shows an alternative embodiment of the second end portion 9 of the forming element with a central, ridge-like raised portion 11, which is elongated in the direction towards the intermediate portion 10 and from which transverse, raised corrugations 13 extend. It can be noted that the height of the central raised portion 11 varies in the longitudinal direction of the forming element 1.

Figure 5:
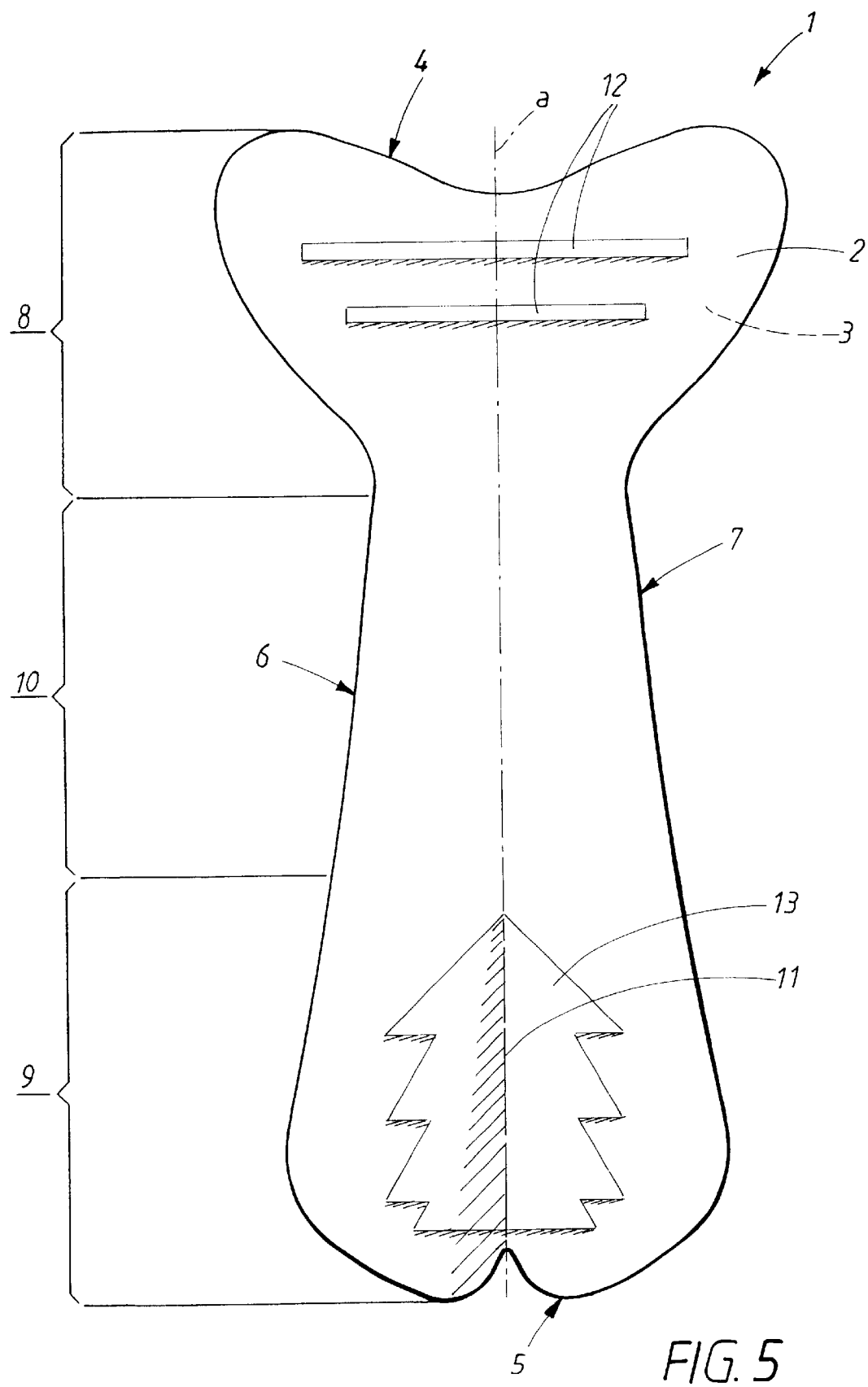
FIG. 5 shows a forming element in accordance with a further embodiment of the invention.

FIG. 5 shows a further embodiment of the invention. FIG. 5 describes a forming element 1 which exhibits corrugations 12 in the form of two elongate raised portions in the first end portion 8 and one corrugation 13 in the form of a symmetrically formed raised area around the ridge-like raised portion 11.

The corrugation 13 has symmetrical protrusions and has approximately the shape of a Christmas tree.

Figure 6:
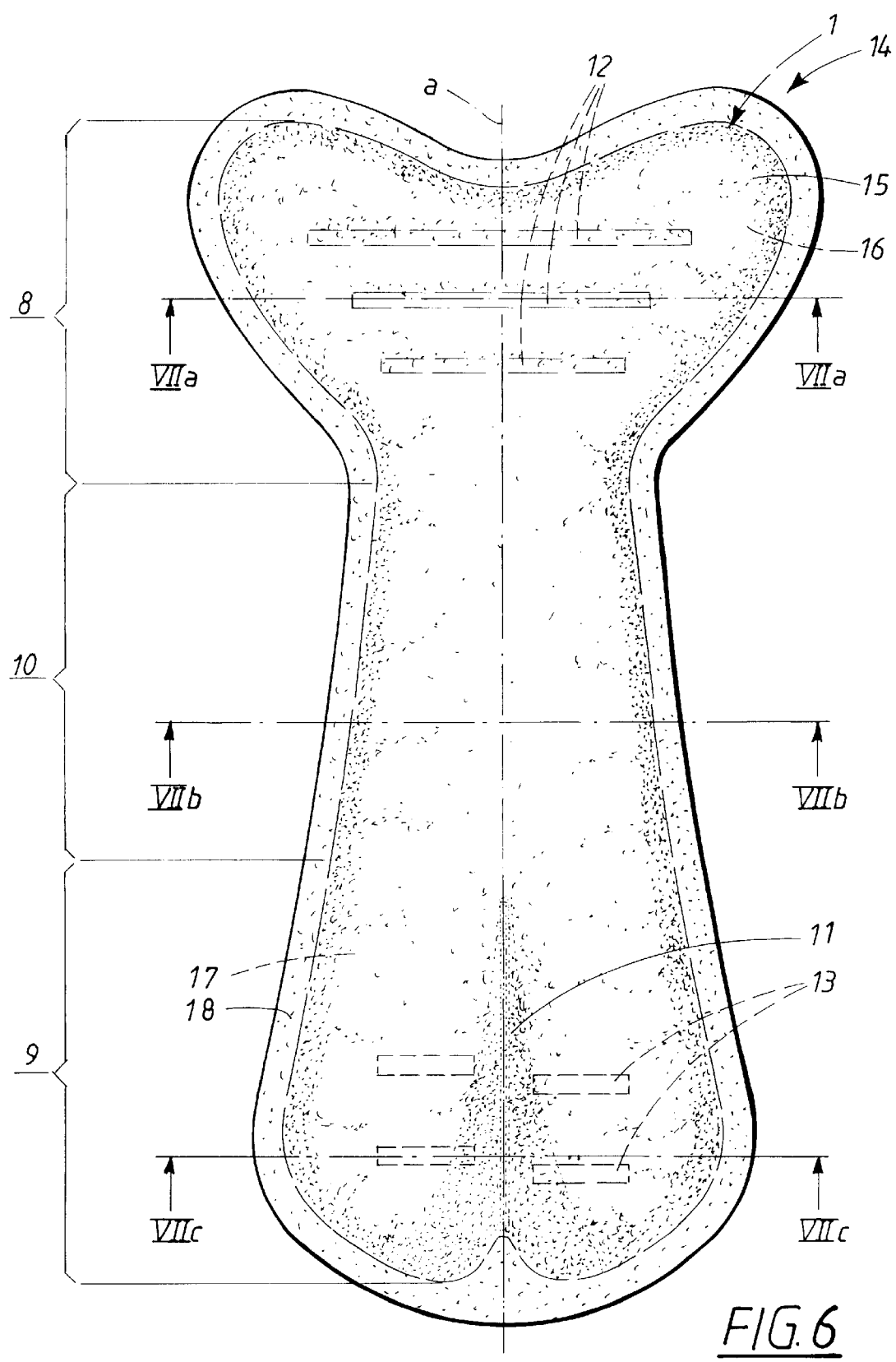
FIG. 6 shows a sanitary napkin in accordance with the invention.

The sanitary napkin 14 shown in FIG. 6 comprises a liquid-permeable surface layer 15 arranged on that side of the sanitary napkin 14 which is intended to face towards the user during use and a liquid-barrier layer 16 arranged on the side of the sanitary napkin 14 which is intended to face away from the user during use. Between the surface layer 15 and the liquid-barrier rear side layer 16 an absorbent layer 17 is arranged.

The material in the surface layer 15 can be, for example, a perforated plastic film, a net of plastic or textile material, a nonwoven material or a laminate of, for example, a perforated plastic layer and a nonwoven layer. The plastic can be a thermoplastic, such as polyethylene. The nonwoven material can comprise natural fibres, such as cellulose or cotton, synthetic fibres, such as polyethylene, polypropylene, polyester, polyurethane, nylon or regenerated cellulose.

The main tasks of the surface layer 15 in the sanitary napkin are to lead liquid in to the absorbent layer 17, to be soft and comfortable against the body of the user and to prevent rewetting, i.e absorbed body fluid penetrating back towards the skin of the user. For reasons of comfort and to avoid skin irritation, it is important that the surface of that part of the sanitary napkin that lies against the skin of the user is maintained as dry as possible during use. Moreover, a dry surface on the sanitary napkin is perceived by the user as cooler and more comfortable during use and is also, purely visually and during handling when the sanitary napkin is to be changed, more attractive than a soiled, wet surface.

The liquid-barrier layer, or rear side layer 16, consists of a liquid-impermeable material. Thin liquid-impermeable plastic films are suitable for the purpose but it is also possible to use material which is initially liquid-permeable but which has been provided with a coating of plastic, resin or other material which resists liquid penetration. By this means, leakage of liquid from the underside of the absorbent article is prevented. The barrier layer 3 can accordingly consist of any material which fulfils the criterion of liquid-impermeability, and also exhibits sufficient skin-friendliness for the purpose. Examples of materials which are suitable as barrier layers are plastic films, nonwovens and laminates of these. The plastic film can be, for example, of polyethylene, polypropylene or polyester. Alternatively, the barrier layer can consist of a laminate of a liquid-impermeable plastic film, facing towards the absorbent body, and a nonwoven material, facing towards the underclothes of the user. Such a construction gives a leakproof barrier layer with a textile feel. It is also possible to use the forming element 1 as a barrier layer. However, it is then suitable to arrange a soft textile or textile-like material layer on the outside of the forming element.

The absorbent layer 17 is suitably manufactured of cellulose pulp. It can originally be in rolls, bales or sheets which during the manufacture of the sanitary napkin are dry defibrated and transferred in fluffed form to a pulp web, sometimes mixed with superabsorbents, which are polymers with the ability to absorb several times their own weight of water or body fluid. An alternative to this is to dry form a pulp web, as is described in WO 94/10956. Examples of other absorbent materials which can be used are various types of natural fibres, such as cotton fibres, peat moss, or the like. Naturally, it is also possible to utilise absorbent synthetic fibres or mixtures of natural fibres and synthetic fibres. Moreover, the absorbent material can contain further components, such as form-stabilising members, liquid-distributing members or binding agents, such as thermoplastic fibres which have been heat-treated to hold together short fibres and particles into a coherent unit. It is also possible to use various types of absorbent foam material in the absorbent layer.

The sanitary napkin 14 exhibits a forming element 1 in accordance with the invention. The forming element exhibits three elongate corrugations 12 in the form of depressions in the first end portion 8 and four elongate corrugations 13, two of which are situated on either side of the ridge-like raised portion 11 and extending principally in the transverse direction of the forming element and the sanitary napkin. The surface layer 15 and the rear side layer 16 are joined in a glued joint 18 outside the edge of the forming element 1 and the absorbent layer 17.

Figure 7A:
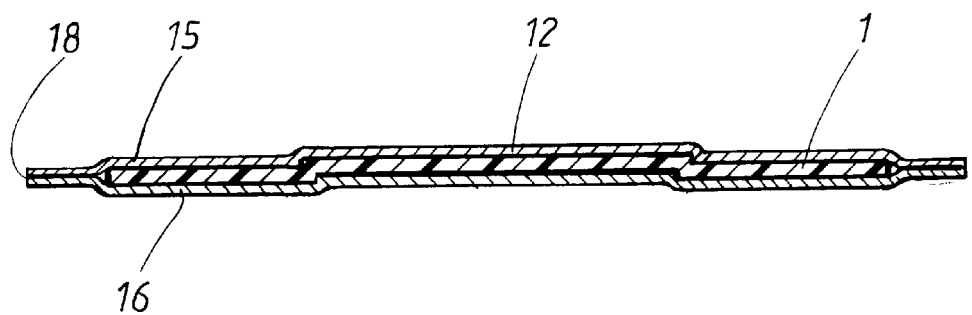
FIG. 7a shows a section along the line VIIa—VIIa through the sanitary napkin in FIG. 6.
Figure 7B:
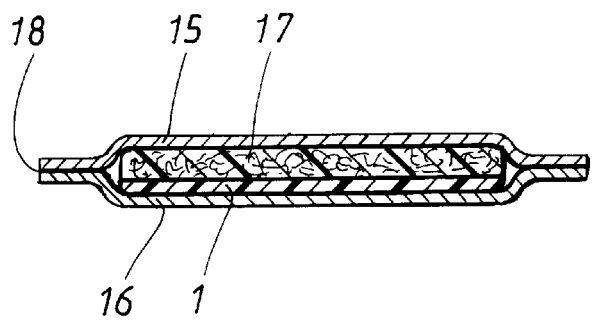
FIG. 7b shows a section along the line VIIb—VIIb through the sanitary napkin in FIG. 6.
Figure 7C:
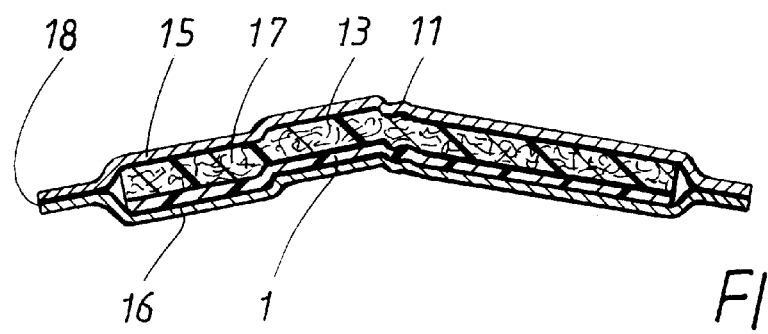
FIG. 7c shows a section along the line VIIc—VIIc through the sanitary napkin in FIG. 6.

FIGS. 7a–c show sections along the lines VIIa—VIIa, VIIb—VIIb and VIIc—VIIc through the sanitary napkin in FIG. 6. Accordingly, FIG. 7 shows the absorbent layer situated in the intermediate portion 10 and the second end portion 9. In the first end portion 8 there are only the surface layer 15, the rear side layer 16 and the forming element 1. Of course, it is possible to arrange the absorbent layer in alternative ways, such as within only the intermediate portion 10, or over the entire sanitary napkin 14.

The described embodiments are merely intended to illustrate the invention and should not be regarded as limiting the invention. For example, it is possible within the framework of the invention to combine all given corrugations in the first and the second end portions with each other.

What is claimed is:

1. A forming element in an absorbent article, which forming element is formed of a rigid material and exhibits a principally elongate form with a longitudinal direction and a transverse direction, an upper side, an underside, two short sides and two long sides, a first and a second end portion and an intermediate portion situated between the end portions, the forming element being formed of a plastic layer having a thickness between approximately 0.2 mm and approximately 0.4 mm, wherein the forming element exhibits at least two corrugations, wherein the corrugations are arranged as elongate raised portions or depressions on the upper side of the forming element and exhibit a longitudinal direction and a transverse direction, wherein the corrugations are arranged with a longitudinal direction of the corrugations being principally in the transverse direction of the forming element, wherein the corrugations have a height or a depth measured from a plane of the forming element which is from about 1.5 mm to 5 mm, a width which is from about 0.3 mm to 10 mm, and a length from about 0.8 mm to 8 cm;

wherein the corrugations are arranged in the first end portion; and wherein the first end portion has a greater width at a first short side of the forming element than at a transition between the first end portion and the intermediate portion, and in that the corrugations are constituted of at least two elongate corrugations which extend transversely over a central part of the first end portion, wherein the corrugations are formed with a shorter length as the corrugations are situated near the intermediate portion of the forming element and exhibit end edges extending in the longitudinal direction of the forming element, and in that edge portions along the two long sides of the forming element at the first end portion are free of corrugations, wherein the end edges of the corrugations define folding lines for the edge portions so that the edge portions can be turned upward with respect to the central part of the first end portion along the folding lines of the forming element and form cupped walls around the central part of the first end portion.

2. A forming element in accordance with claim 1, further comprising a ridge-like raised portion arranged on the upper side of the forming element in the longitudinal direction of the forming element in the second end portion.

3. A forming element in accordance with claim 1, wherein the corrugation-free edge portions of a forward end portion have a width between the end edges of the corrugations and the long sides of the first end portion that is at least about 5 mm.

4. A forming element in accordance with claim 3, wherein the corrugation-free edge portions of the forward end portion have a width between the end edges of the corrugations and the long sides of the first end portion that is between about 7 mm and 25 mm.

5. A forming element in accordance with claim 1, wherein the corrugations are arranged in the second end portion, which is intended to face backwards on a user during use.

6. A forming element in accordance with claim 1, wherein the corrugations are arranged as raised portions from the upper side of the forming element.

7. A forming element in accordance with claim 1, wherein the corrugations are arranged as depressions from the upper side of the forming element.

8. A forming element in accordance with claim 1, wherein the corrugations are arranged as raised or depressed areas with a regular or irregular form and with a surface of about $5 \times 3$ cm$^2 \pm 5$ cm$^2$ on the upper side of the forming element.

9. A forming element in accordance with claim 1, wherein the widest part of the first end portion is 1.5–5 times as wide as the narrowest width on the intermediate portion.

10. An absorbent article, which has a principally elongate form with two end portions and an intermediate portion situated between the end portions, wherein the article comprises a forming element in accordance with claim 1.

11. An absorbent article in accordance with claim 10, wherein said absorbent article comprises a sanitary napkin.

12. An absorbent article in accordance with claim 10, wherein said absorbent article comprises an incontinence protector.

13. An absorbent article in accordance with claim 10, wherein said absorbent article comprises a panty shield.

14. A forming element in accordance with claim 1, wherein the width is about 0.5 mm.

15. A forming element in accordance with claim 1, wherein the intermediate portion is essentially free of corrugations.

16. A forming element in accordance with claim 1, wherein the corrugations are arranged only in at least one of the first and second end portions.

17. A forming element in accordance with claim 1, wherein the corrugations are arranged to increase a bending resistance of the forming element and thereby preserve a desired pre-determined shape of the forming element.

* * * * *